(12) United States Patent
Holderby et al.

(10) Patent No.: US 11,116,626 B2
(45) Date of Patent: Sep. 14, 2021

(54) IOL INJECTOR HAVING A LEVER-DRIVEN PLUNGER MECHANISM

(71) Applicant: Alcon Inc., Fribourg (CH)

(72) Inventors: Victoria Holderby, Arlington, TX (US); Jian Liu, Keller, TX (US); Rudolph F. Zacher, Trabuco Canyon, CA (US)

(73) Assignee: Alcon Inc.

( * ) Notice: Subject to any disclaimer, the term of this patent is extended or adjusted under 35 U.S.C. 154(b) by 173 days.

(21) Appl. No.: 16/454,477

(22) Filed: Jun. 27, 2019

(65) Prior Publication Data

US 2020/0197159 A1    Jun. 25, 2020

Related U.S. Application Data

(60) Provisional application No. 62/781,736, filed on Dec. 19, 2018.

(51) Int. Cl.
*A61F 2/16*    (2006.01)

(52) U.S. Cl.
CPC ............ *A61F 2/167* (2013.01); *A61F 2/1678* (2013.01); *A61F 2002/1681* (2013.01)

(58) Field of Classification Search
CPC ...... A61F 2/167; A61F 2/1678; A61F 2/1662; A61F 2/1667; A61F 2/1672; A61F 2/1675; A61F 2/1691; A61F 2/2436; A61F 2002/1681; A61F 2002/1682; A61F 2002/16903; A61F 2002/16905; A61F 2002/169051; A61F 2002/169052; A61F 2002/16053
See application file for complete search history.

(56) References Cited

U.S. PATENT DOCUMENTS

| | | |
|---|---|---|
| 2004/0243141 A1 | 12/2004 | Brown et al. |
| 2014/0135784 A1 | 5/2014 | Maroscheck et al. |
| 2016/0256316 A1 | 9/2016 | Van Noy et al. |
| 2017/0245984 A1* | 8/2017 | Germann ................ F16H 19/04 |
| 2017/0360556 A1 | 12/2017 | Auld |

FOREIGN PATENT DOCUMENTS

| | | |
|---|---|---|
| EP | 2653134 A1 | 10/2013 |
| EP | 3210573 A1 | 8/2017 |
| WO | WO2013159045 A1 | 10/2013 |

\* cited by examiner

*Primary Examiner* — Erich G Herbermann (57) ABSTRACT

An IOL injector having a lever-driven plunger mechanism is described.

19 Claims, 12 Drawing Sheets

IOL INJECTOR HAVING A LEVER-DRIVEN PLUNGER MECHANISM

CROSS-REFERENCE TO RELATED APPLICATIONS

This application claims priority to U.S. Provisional Application Ser. No. 62/781,736, filed on Dec. 19, 2018, the contents of which is incorporated herein by reference in its entirety.

TECHNICAL FIELD

The present disclosure relates to systems, apparatuses, and methods for intraocular lens (IOL) injectors.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape, and length of the eye, and the shape and transparency of the cornea and lens. When trauma, age, or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens (IOL).

Many cataractous lenses are removed by a surgical technique called phacoemulsification. During this procedure, an opening is made in the anterior capsule of an eye and a phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced with an IOL.

SUMMARY

An intraocular lens (IOL) injector having a lever-driven plunger mechanism is described. The IOL injector includes an injector body having a bore having a longitudinal axis extending from the proximal end of the injector body to a distal end of the injector body. The injector body includes a rail disposed on an interior wall of the injector body, the rail aligned with the longitudinal axis and extending into the bore. The IOL injector also includes a plunger movably coupled within the injector body and aligned within the bore, and a track disposed within the plunger, the track adapted to be axially slidably coupled with the rail and adapted to prevent rotation of the plunger around the longitudinal axis. The IOL injector also has a lever having a first end having a handle accessible to a user and a second end rotatably coupled to the injector body, a rack having one or more teeth, the rack coupled to the lever, and a nut coupled with the injector body such that the nut is adapted to rotate around the plunger, but not move axially relative to the injector body. The nut is disposed within the bore and has an inner surface adapted to rotatably couple with the thread of the plunger, and an outer surface having one or more teeth disposed around a circumference of the outer surface and forming a pinion. The one or more teeth of the pinon are adapted to mesh with the one or more teeth of the rack. In response to a force applied to the handle, the lever is adapted to rotatably move from a resting position, the rack is adapted to move and mesh with the pinion disposed on the nut, the nut is adapted to rotate in a first rotational direction, and thereby rotatably move along the thread of the plunger, the track of the plunger is adapted to engage with the rail of the injector body and thereby prevent rotation of the plunger around the longitudinal axis, and in response, the plunger is adapted to move axially through the bore.

The IOL injector may include a return spring having a first end coupled to the lever and a second end coupled to the injector body. In response to the force applied to the handle, the return spring may be adapted to return the lever to the resting position.

The one or more teeth of the rack may be adapted to engage the one or more teeth of the pinion and to rotate the pinion only in response to the movement of the lever away from the resting position.

The one or more teeth of the rack may form one or more pawls and the one or more teeth of the pinion may form a ratchet.

The one or more teeth of the rack may form a ratchet and the one or more teeth of the pinion may form a pawl.

The injector body may include a tooth-engaging ridge adapted to contact the one or more teeth of the pinion and prevent rotational movement of the pinion in a second rotational direction opposite to the first rotational direction.

The inner surface of the nut may include a thread adapted to rotatably engage with the thread of the plunger.

The inner surface of the nut may include one or more thread-engaging pins adapted to rotatably engage with the thread of the plunger.

The plunger may include a non-threaded portion adapted to slidably move through the nut in response to an axial force applied to the plunger.

A proximal portion of the plunger may be accessible to a user, and the plunger may be adapted to move axially in response to an axial force applied to the plunger.

The injector body may include an IOL storage location configured to house an IOL, and an IOL dwell location distal to the IOL storage location.

The plunger may include a non-threaded portion adapted to slidably move through the nut in response to an axial force applied to the plunger. The plunger may be adapted to move axially from a first position proximally adjacent to the IOL storage location to a second position proximally adjacent to the dwell location in response to an axial force applied to the plunger. The plunger may be adapted to move axially from the second position to the distal end of the injector body in response to a force applied to the handle.

The plunger may be adapted to move axially from a first position proximally adjacent to the IOL storage location to the distal end of the injector body in response to one or more depressions of the lever.

The plunger may be axially movable from the second position to the distal end of the injector body in response to one or more depressions of the lever.

The plunger thread may have a pitch that varies along the longitudinal axis of the plunger.

The plunger thread may have a pitch that is longer toward a proximal end of the plunger than toward a distal end of the plunger.

The IOL injector may be adapted for single-handed operation by a user.

The IOL injector may be adapted to separately inject an IOL base, an IOL optic, or both.

The IOL injector may be adapted to concurrently inject an IOL base and an IOL optic.

BRIEF DESCRIPTION OF THE DRAWINGS

For a more complete understanding of the present disclosure, reference is now made to the following description, taken in conjunction with the accompanying drawings, which are not to scale, and in which.

DETAILED DESCRIPTION

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Figure 1:
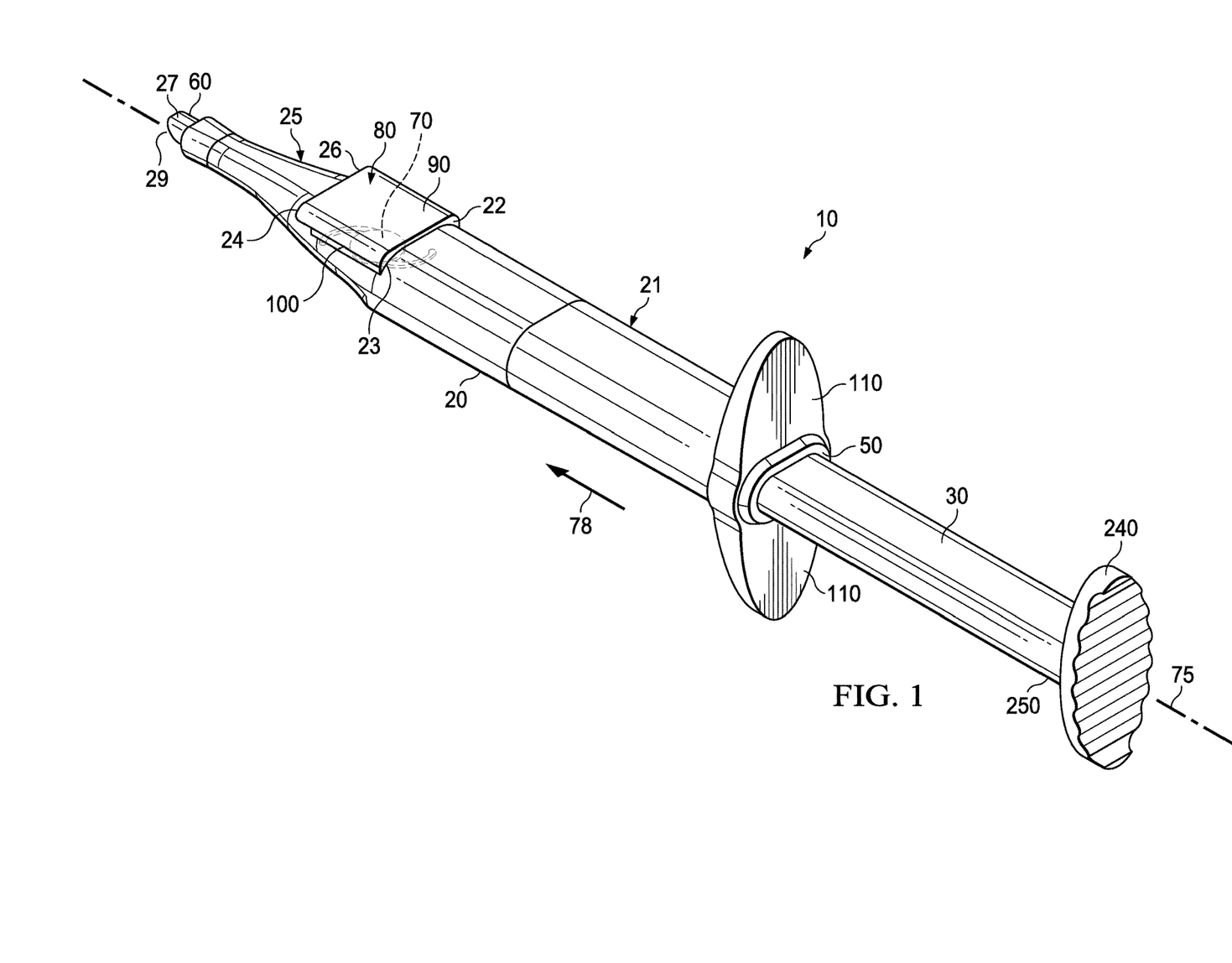
FIG. 1 is a perspective view of an example IOL injector.
Figure 2:
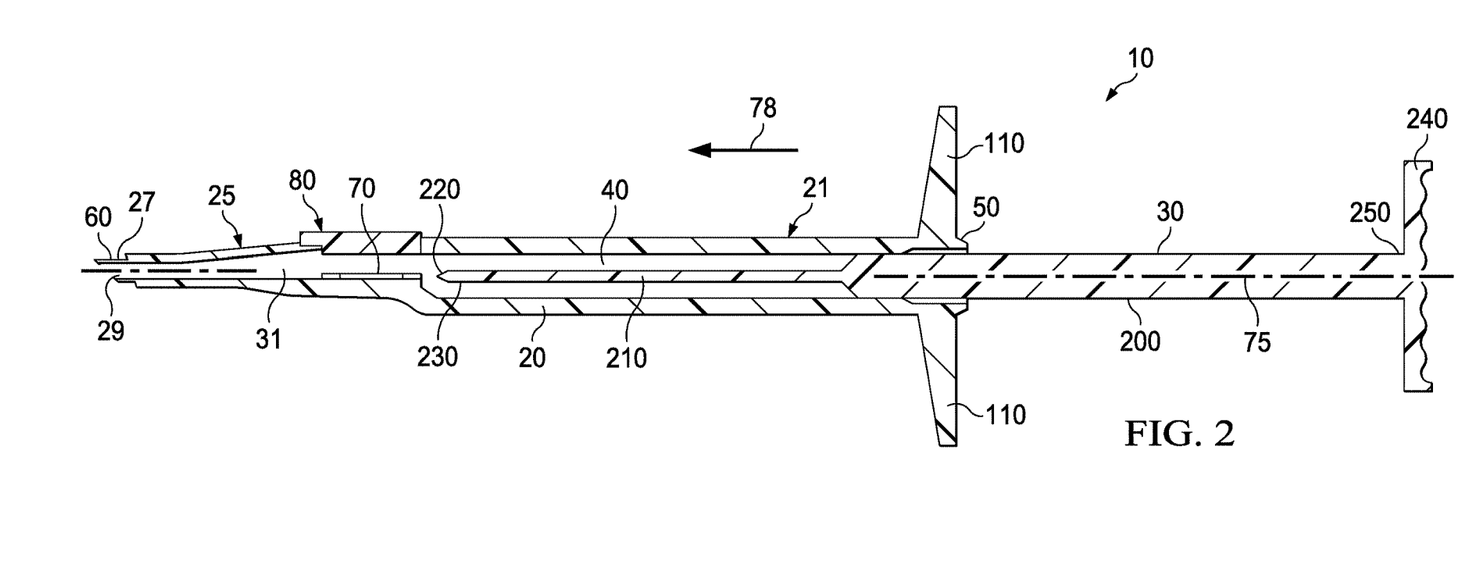
FIG. 2 is a longitudinal cross-sectional view of the example IOL injector of FIG. 1.

FIGS. 1 and 2 are schematics of an example IOL injector 10 that is actuated by manual user application of force. The IOL injector 10 includes an injector body 20, a plunger 30 adapted to reciprocate through a bore 40 formed in the injector body 20. The injector body 20 has a main body 21 having a proximal end 50 and a distal end 23, and a nozzle 25 having a proximal end 22 and a distal end 60. The proximal end 22 of the nozzle 25 is coupled to the distal end 23 of the main body 21. The nozzle 25 has an IOL storage location 80 configured to house an uncompressed IOL 70, and an IOL dwell location 809 distal to the IOL storage location 80.

The bore 40 extends from the proximal end 50, or a proximal portion thereof, of the main body 21 to the distal end 60 of the nozzle 25. A distal portion of the bore 40 within the nozzle 25 forms a tapered delivery channel 31 through which an IOL may be axially advanced, compressed, and delivered into an eye via an opening 29 in distal tip 27 at distal end 60.

The plunger 30 is movably coupled within the injector body 20 and aligned within the bore 40. The plunger 30 has a plunger tip 220 adapted to contact an IOL 70.

The IOL injector 10 also includes a longitudinal axis 75. The longitudinal axis 75 may extend along the plunger 30 and define a longitudinal axis of the plunger 30.

The IOL storage location 80 may include a door 90 to provide access to the interior of the IOL storage location 80. The door 90 may include a hinge 100 such that the door 90 may be pivoted about the hinge 100 to open the IOL storage location 80 and, for example, allow the installation of the IOL 70. In other implementations, the IOL storage location 80 may exclude a door for installing the IOL 70. In such instances, the IOL 70 may be incorporated into the IOL storage location 80 at the time of assembly of the IOL injector 10. Thus, in such instances, the IOL injector 10 would be a preloaded IOL injector. In such instances, the IOL storage location 80 may have a cover that is not configured to open, rather than a door 90. The IOL storage location 80 may include a hole adapted to allow addition of viscoelastic into the IOL storage location 80.

The injector body 20 may also include tabs 110 formed at the proximal end 50 of the injector body 20. The tabs 110 may be manipulated by fingers, thumb, or hand of a user, such as an ophthalmologist, an ophthalmic surgical assistant or nurse, or other medical professional, to advance the plunger 30 through the bore 40.

The plunger 30 may include a plunger body 200, a plunger rod 210 extending distally from the plunger body 200, and a plunger tip 220 formed at the distal end 230 of the plunger rod 210 and adapted to contact an IOL disposed, for example, with the IOL storage location 80 of the IOL injector 10. As the plunger 30 is axially advanced and thereby displaced distally within the bore 40 in the direction of the arrow 78, the plunger tip 220 of the plunger 30 is adapted to engage and advance the IOL, such as IOL 70. In FIGS. 1 and 2, the IOL 70 is shown located within the IOL storage location 80. The plunger 30 may also include flanges 240 formed at proximal end 250, which may be manipulated by the fingers, thumb, or hand of a user to advance the plunger 30 through the bore 40 by displacing the plunger 30 through the bore 40 distally in the direction of the arrow 78.

Figure 3A:
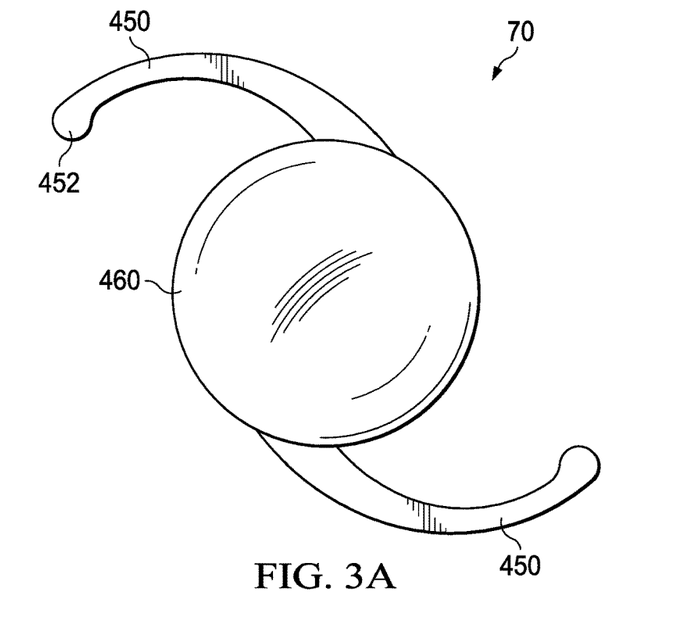
FIG. 3A shows an example one-piece IOL.

In some implementations, the IOL 70 may be a one-piece IOL. That is, in some implementations, the IOL 70 may include an optic 460 and haptics 450, as shown in FIG. 3A. Each of the haptics 450 include a tip 452. In some implementations, the optic 460 and the haptics 450 may be integrally formed out of a single piece of material. In other implementations, the optic 460 may be formed out of one piece of material; the haptics 450 may be formed out of another piece of material, and the optic 460; and the haptics 450 may be coupled together prior to delivery into an eye. In some instances, the optic 460 and haptics 450 may be fixedly secured to each other prior to insertion into an IOL injector and delivered into an eye.

Figure 3B:
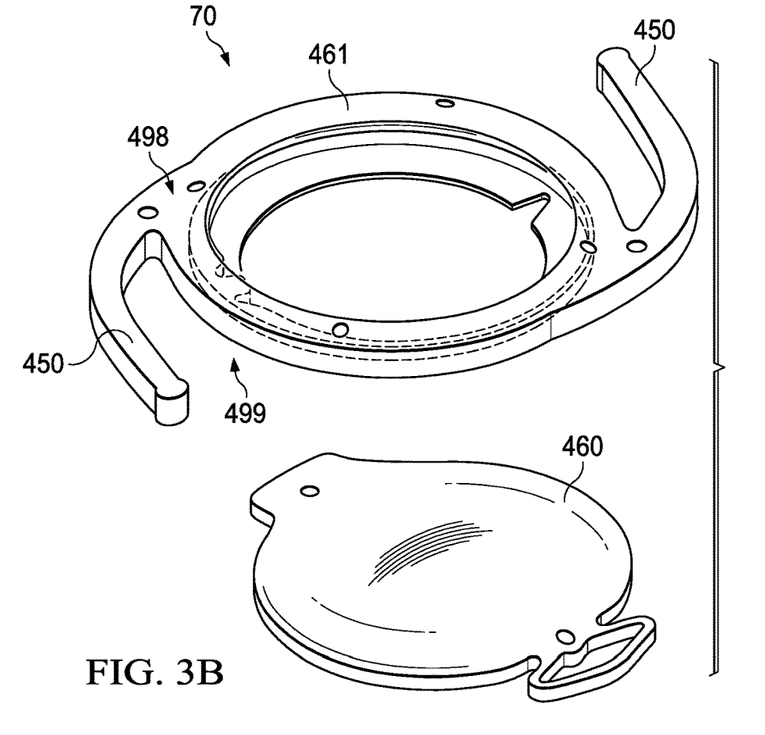
FIG. 3B shows an example two-piece IOL including a base and an optic.
Figure 4:
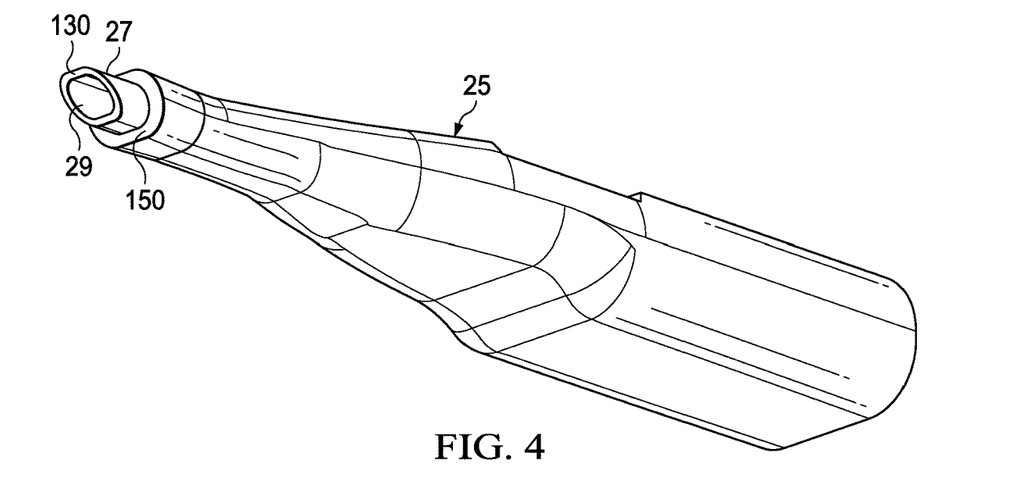
FIG. 4 is a perspective view of an example nozzle of an IOL injector.
Figure 5A:
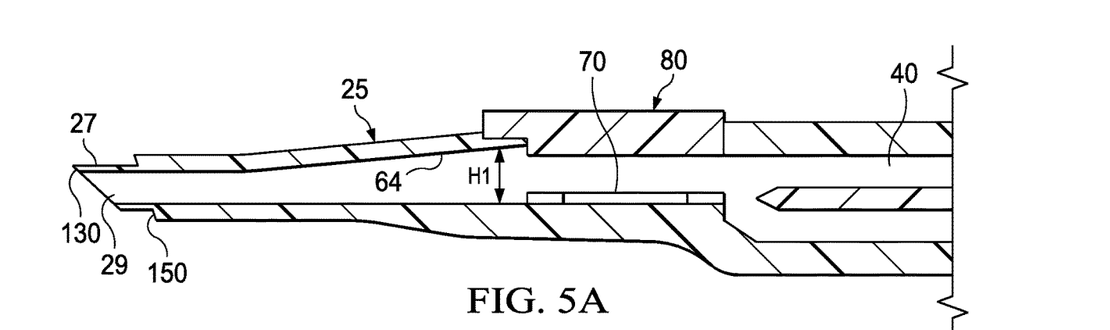
FIG. 5A is a cross-sectional view of the nozzle of the IOL injector of FIG. 4.
Figure 5B:
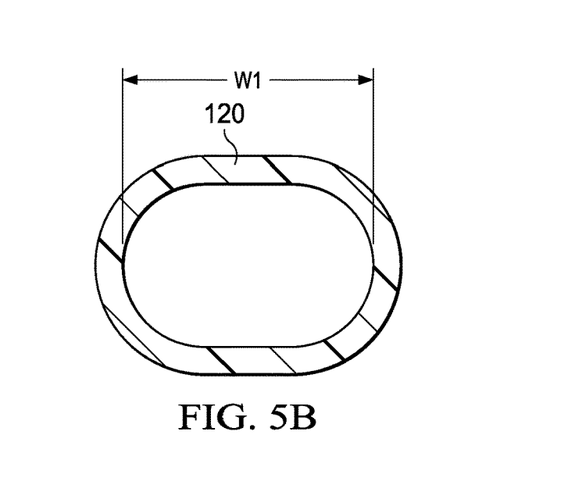
FIG. 5B is another cross-sectional view of the nozzle of the IOL injector of FIG. 4.

In other implementations, the IOL 70 may be a multi-piece IOL, as shown, for example, in FIG. 3B. For example, in some implementations, the IOL 70 be include two or more separate components. FIG. 3B is an example IOL 70 that includes two removably attached components. As shown in FIG. 3B, the IOL 70 includes an optic 460 and a base 461 that includes haptics 450 and that has a top 498 and a bottom 499. The optic 460 and the base 461 are adapted to be coupled together into a unitary IOL and, thereafter, detached from each other into separate components, if desired. In some instances, one or more components of a multi-piece IOL, such as, for example the two-piece IOL 70 shown in FIG. 3B, are separately injectable into a patient's eye. Once in the eye, the components may be assembled into a complete IOL. For example, in the case of the two-piece IOL 70 shown in FIG. 3B, the optic 460 and the base 461 are separately injectable into an eye. Once injected, the optic 460 is adapted to be coupled to the base 461.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 70 may be a two-piece IOL wherein the base 461 and the optic 460 are separately injected into the patient's eye. Accordingly, for two-piece IOLs, the base 461 and the optic 460 may be contained in separate IOL injectors 10 for insertion in the eye. In other implementations, the two components of a two-piece IOL may be inserted into an eye separately using a single IOL injector. For a single piece IOL, the optic 460 and haptics 450 form a unitary IOL and are inserted into an eye simultaneously with the use of a single IOL injector.

Accordingly, in some implementations, a user may place a one-piece IOL into an IOL injector, for example, by loading an IOL into an IOL storage compartment of the IOL injector, such as the IOL storage location 80 of the IOL injector described above. As also explained, the IOL storage location 80 may be accessed via a door, such as the door 90.

In the case of a two-piece IOL, in some implementations, a user may load the base, such as base 461, into an IOL storage compartment of an IOL injector, for example, via a door. The optic such as optic 460, may be introduced into the IOL storage compartment of a separate IOL injector, for example, via a door. In some instances, the IOL storage compartment may be accessed through the door such as door 90.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed in the IOL injector before and is already contained within the IOL injector when the IOL injector is received by the user. The IOL injector(s) may be packaged within sterile packaging when received by a user.

As would be understood by persons of ordinary skill in the art upon reading the present disclosure, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. For example, manual installation and folding of an IOL may also introduce the possibility of contamination of the IOL, such as by human error or poor sterile technique. Contamination of the IOL may compromise the sterile environment for the patient and risk infection or other harm to the patient.

FIGS. 4-7 illustrate details of the example nozzle 25. In some instances, the nozzle 25 has a tapered exterior surface. Further, the nozzle 25 may include a portion of the bore 40 forming a tapered delivery channel 31 that tapers towards the opening 29. The distal tip 27 is adapted for insertion into an eye so that the IOL 70 may be implanted. The IOL 70 is expelled from the opening 29 formed in the distal tip 27 into the eye. As shown in FIG. 5B, tapered delivery channel 31 and the distal tip 27 may have an elliptical cross section 120 having a width W1. Additionally, the distal tip 27 may include a beveled tip 130. The IOL storage location 80, delivery channel 31, and opening 29 may define a delivery passage. A size of the delivery passage may vary along its length. For example, in some instances, the width W1, a height H1, or both, of the delivery passage may change along a length of the delivery passage. The variation in size of the delivery passage may contribute to the compression of the IOL as it is advanced therealong through the delivery passage.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the distal tip 27 is permitted to extend into an eye, as described in U.S. application Ser. No. 15/049,315, the disclosure of which is being incorporated herein by reference in its entirety.

Figure 6:
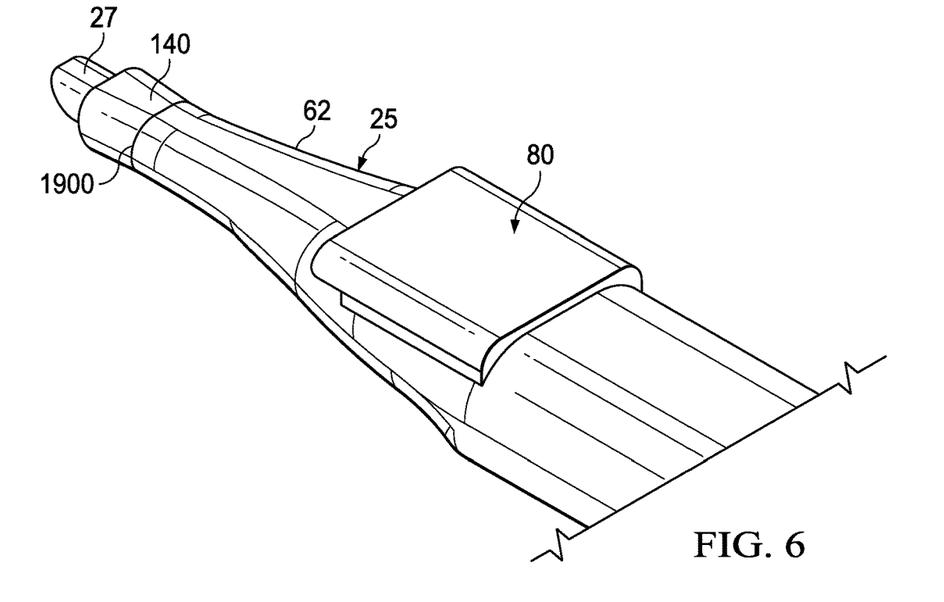
FIG. 6 is another perspective view of the nozzle of the IOL injector of FIG. 4.
Figure 7:
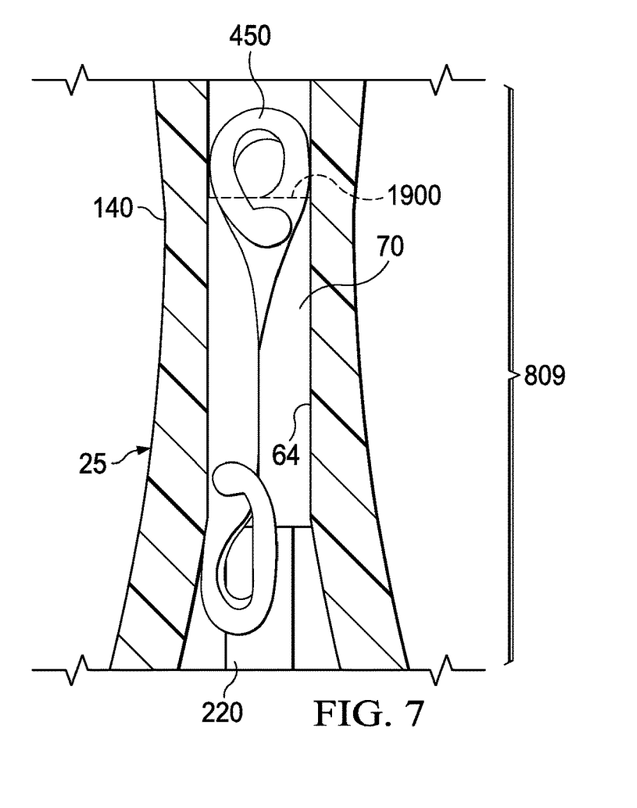
FIG. 7 is a view of a distal end of an example IOL injector with an IOL located therein and positioned in a dwell location.

FIG. 6 and FIG. 7 are detail views of a portion of the example nozzle 25. The nozzle 25 may include a tapered portion 62 and the insertion depth guard 140. The distal tip 27 may include a demarcation 1900 that provides a visual indication of a dwell location 809 of a compressed or partially compressed IOL 70. The term "dwell location" as used herein refers to a location adjacent to the distal end 60 of the nozzle 25. For example, the dwell location 809 may be a location 2-10 mm from the distal end 60. For example, in the example shown in FIG. 6, the demarcation 1900 is a narrow ridge or line that encircles all or a portion of the nozzle 25. In some instances, the demarcation 1900 may be disposed between the tapered portion 62 and the insertion depth guard 140. At least a portion of the injector body 20 may be formed from a transparent or semi-transparent material that permits a user to see an IOL within the injector body 20. Particularly, the nozzle 25 of the injector body 20 may be formed from a transparent material to permit observation of the IOL as it is moved therethrough by the plunger 30.

FIG. 7 shows a view of the distal end 60 of the IOL injector 10 with an IOL 70 located therein at a dwell position 809 in nozzle 25. As shown in FIG. 7, the dwell position 809 of the IOL 70 may be defined as a location where a distal edge of the optic of the IOL 70 substantially aligns with the demarcation 1900. A haptic 450 or a portion thereof may extend beyond the demarcation 1900.

Due to the sensitivity and delicacy of ocular tissues and structures, it is important that the user is able to deliver the IOL to a patient's eye with acceptable peak speed and applied actuation force.

Typically, the mechanism of compressing and advancing the IOL by existing IOL injectors involves substantial variation in force required to advance the plunger through the IOL injector. For example, during actuation of existing IOL injectors, there is typically a peak resistance to IOL advancement when the IOL is fully compressed within the nozzle, which is followed by a pressure release when the IOL is at the exit of the nozzle. In some cases, this can cause the IOL to be ejected with high velocity in a less controllable manner. The IOL advancement resistance force peaks and troughs associated with some existing IOL injectors can reduce user control of the IOL injector and the IOL delivery. The challenges of delivering the IOL include, for example, ensuring that the mechanism and magnitude of force applied through user actuation of the IOL injector is appropriate and repeatable. It is also preferable to have an IOL injector that is intuitive to use and can be utilized by users of the entire spectrum of skills and techniques.

In various implementations described herein, the present disclosure relates to a lever-driven plunger mechanism adapted to solve the problems described above. Advantages of the lever-driven plunger mechanism described herein include, without limitation providing a consistent actuation force experience for the user, preventing sudden IOL ejection, providing higher reliability and comfort for the user, with improved safety.

FIG. 8A-FIG. 11 are schematics of IOL injectors having various example implementations of the lever-driven plunger mechanism of the present disclosure.

An IOL injector 10 having a lever-driven plunger mechanism of the present disclosure has an injector body 20, which may include a main body 21 and a nozzle 25 coupled to the distal end 23 of the main body 21, and a bore 40 having a longitudinal axis 75 extending from the proximal end 50 of the main body 21 to the distal end 60 of the nozzle 25.

As shown for example in FIG. 8A-FIG. 8D, in some implementations, the IOL injector 10 has a lever-driven plunger mechanism that includes one or more rails 1301 disposed on an interior wall 1203 of the injector body and aligned with the longitudinal axis 75 and extending into the bore 40.

Typically, the lever-driven plunger mechanism may include two rails 1301 disposed on opposite sides, such as opposite lateral sides, of an interior wall 1203 of the injector body, such as within opposite lateral sides of the bore 40. The rails 1301 may be typically parallel to each other and aligned with the longitudinal axis 75. The rails 1301 may extend from the proximal end 50 of the main body 21 to the distal end 60 of the nozzle 25, or a portion thereof.

The lever-driven plunger mechanism also includes a plunger 30. The plunger 30 may have a plunger rod 210 having a proximal end and a distal end 230, the proximal end of the plunger rod 210 coupled to the distal end of the plunger body 200, and a plunger tip 220 formed at the distal end 230 of the plunger rod 210 and adapted to contact an IOL 70 and axially move the IOL 70 in response to actuation of the lever-driven plunger mechanism described herein.

The lever-driven plunger mechanism has one or more tracks 1302 disposed within the plunger 30, such as within the plunger body 200. As shown for example in FIG. 11, the one or more tracks 1302 are adapted to be slidably coupled with the one or more rails 1301 disposed on the interior wall 1203 of the injector body, and thereby adapted to prevent rotation of the plunger 30 around the longitudinal axis 75, for example as shown in the direction of arrow 76 in FIG. 11. Typically, the plunger 30 may have a pair of tracks 1302 disposed on opposite sides of the plunger 30, such as opposite lateral sides, of the plunger body 200. The tracks 1302 may be typically parallel to each other and aligned with the longitudinal axis 75. The tracks 1302 may extend from the proximal end of the plunger 30 to the distal end of the plunger 30, or a portion thereof.

The plunger 30 also has a threaded portion having a thread 1 disposed within the plunger 30, such as within the plunger body 200. As would be understood by skilled persons, the term "thread" as used herein, also known as a "screw thread", generally refers to an inclined plane wrapped around a longitudinal axis. Typically, a thread is a helical structure used to convert between rotational and linear movement or force. A thread is typically a ridge wrapped around a cylinder in the form of a helix. In implementations described herein, the threaded portion of the plunger 30 has a thread 1 wrapped around the longitudinal axis of the plunger 30.

Figure 8A:
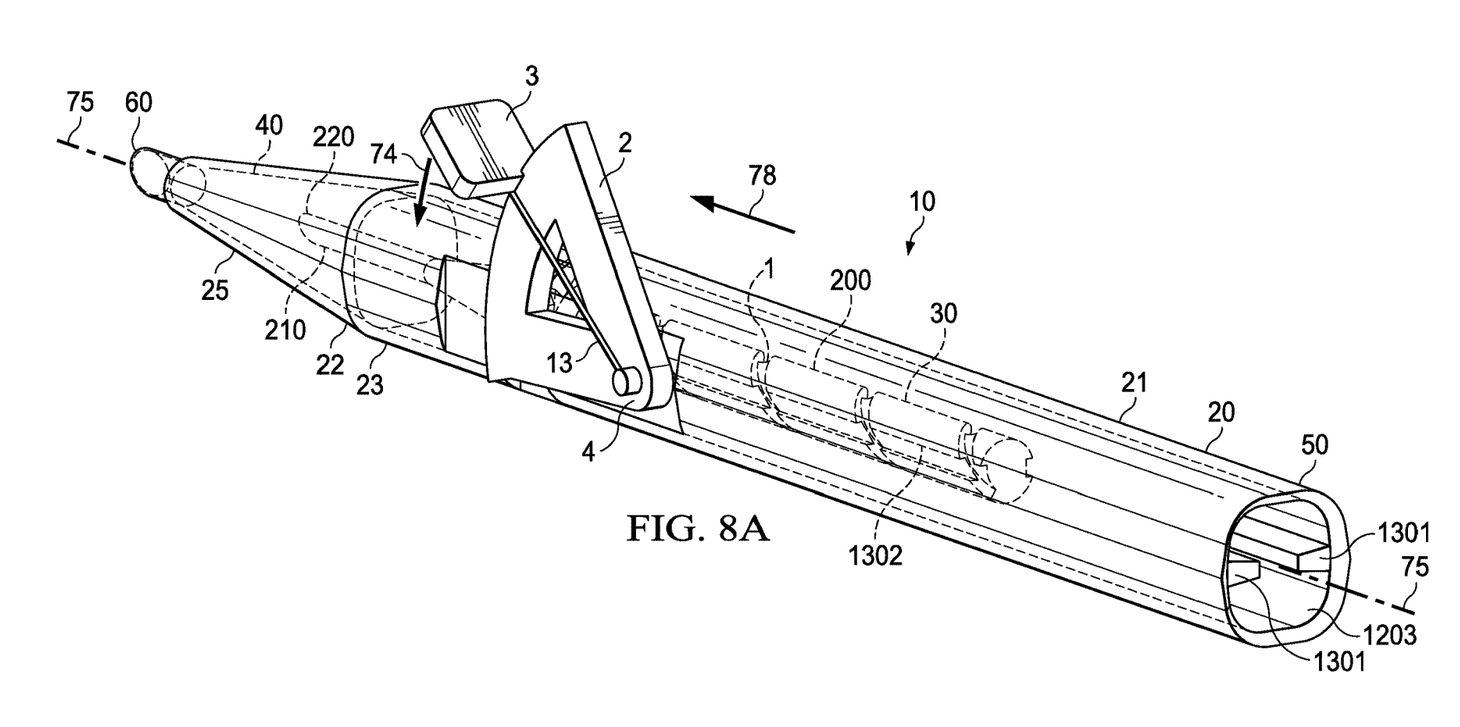
FIG. 8A is a schematic of an example IOL injector having a lever-driven plunger mechanism.
Figure 8B:
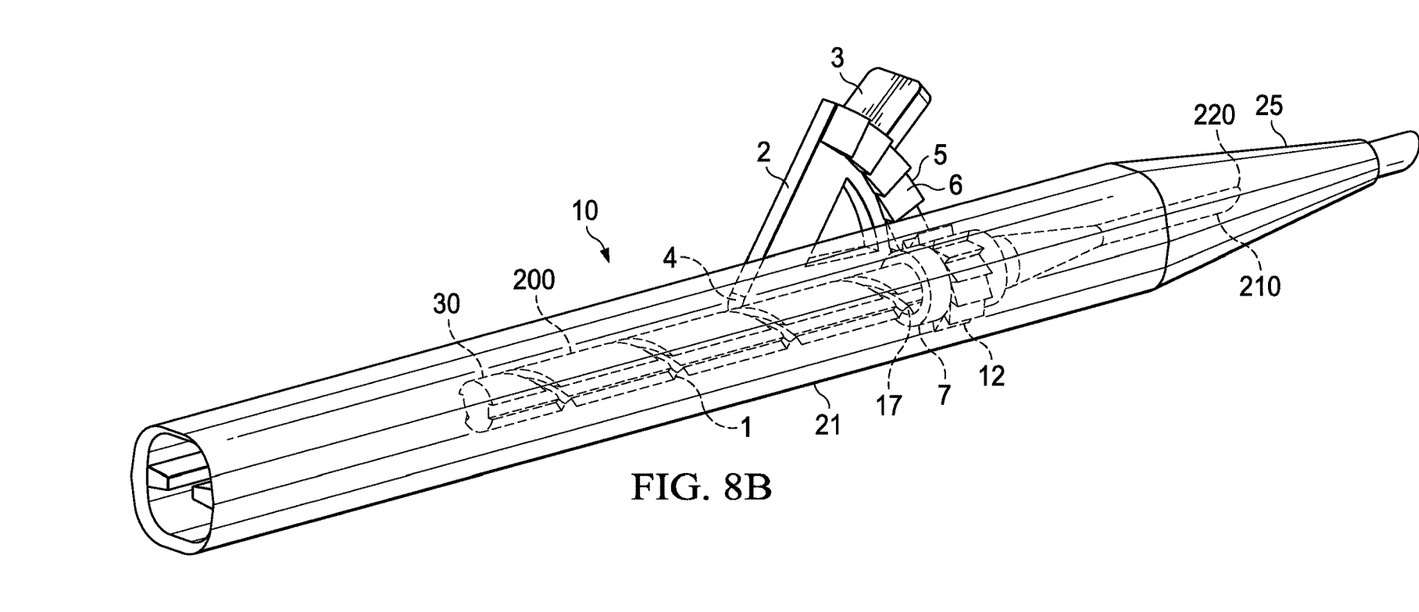
FIG. 8B is another view of the example IOL injector of FIG. 8A.
Figure 8C:
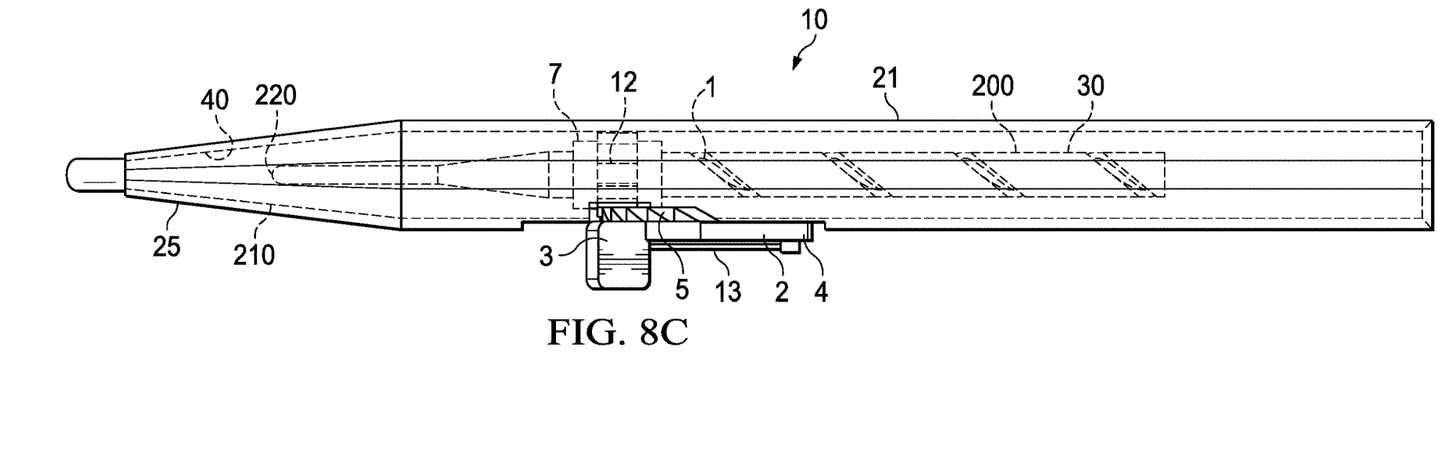
FIG. 8C is another view of the example IOL injector of FIG. 8A.
Figure 8D:
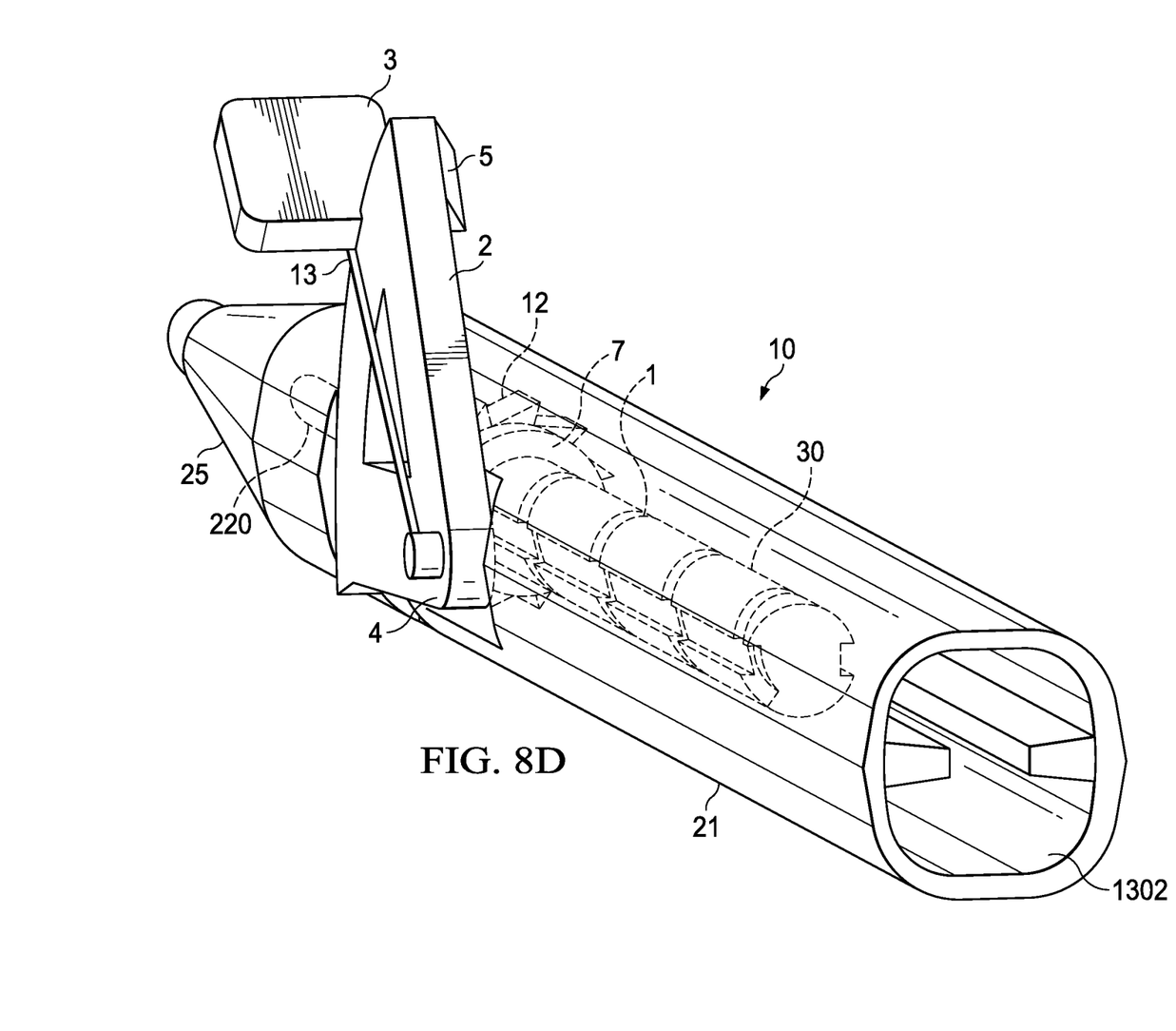
FIG. 8D is another view of the example IOL injector of FIG. 8A.

The lever-driven plunger mechanism is adapted to axially advance the plunger 30, such as shown for example in the direction of arrow 78 in FIG. 8A, in response to depression of a lever 2, such as shown for example in the direction of arrow 74 in FIG. 8A. For example, as shown in FIG. 8A-FIG. 8D, the lever-driven plunger mechanism includes a lever 2 having a first end and a second end 4. The first end of the lever 2 includes a handle 3 accessible to a user and a second end 4 rotatably coupled to the injector body 20. The lever-driven plunger mechanism also has a rack 5, such as an arcuate rack 5, having one or more teeth 6. The rack 5 is coupled to the lever 2. In particular, the rack 5 may be an arcuate rack 5 coupled to the lever such that upon depression of the handle 3, the lever 2 is adapted to rotate through an arc corresponding to the arc of the arcuate rack 5.

Figure 9A:
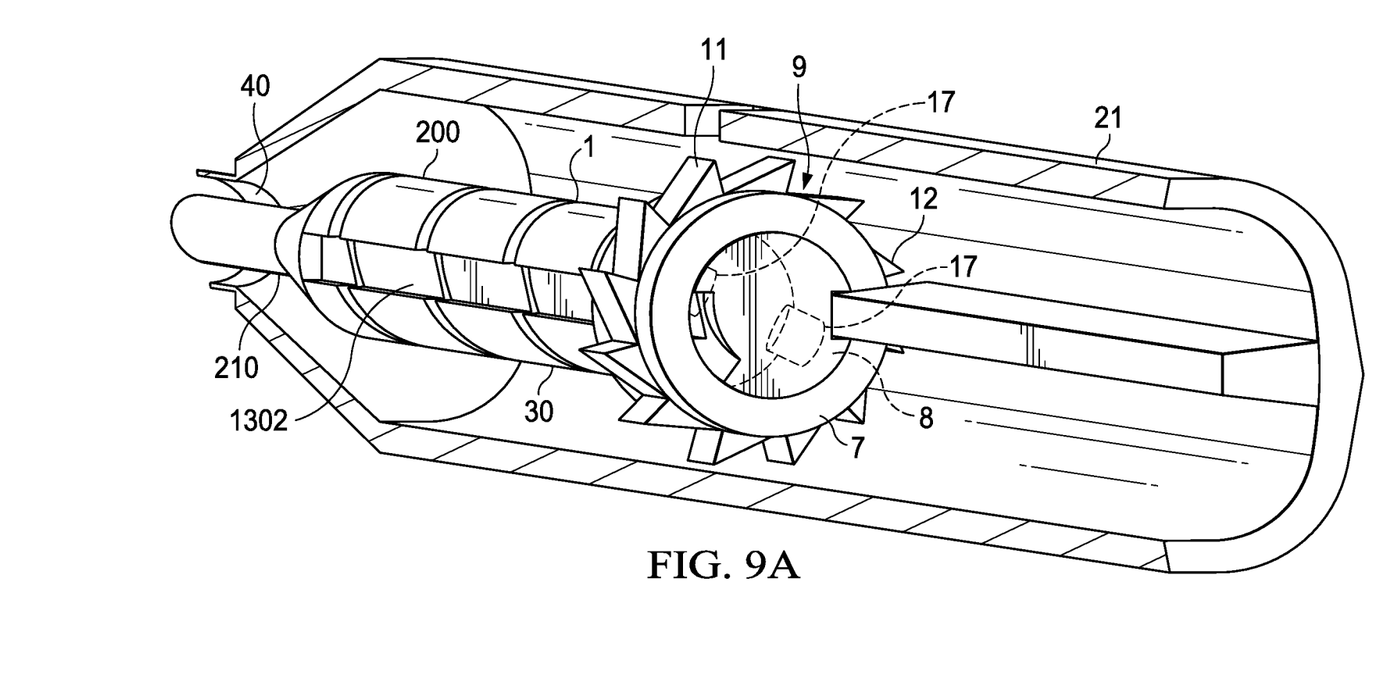
FIG. 9A is a schematic of an example plunger and plunger advancement mechanism.

The lever-driven plunger mechanism also includes a nut 7 coupled with the injector body 20 such that the nut 7 is adapted to rotate around the longitudinal axis 75 of the injector body 20, but not move axially relative to the injector body 20. Further details of the nut 7 are shown in FIG. 9A. The nut 7 is disposed within the bore 40 and the nut 7 has an inner surface 8, adapted to rotatably couple with the thread 1 of the plunger 30. For example, inner surface 8 of the nut 7 may include a thread adapted to rotatably couple with the thread 1 of the plunger 30. In some implementations, the inner surface 8 of the nut 7 may include only a portion of a thread adapted to rotatably engage with the thread 1 of the plunger 30, such as one or more thread 1-engaging pins 17, for example as shown in FIG. 9A and described herein.

The nut 7 also has an outer surface 9 having one or more teeth 11 disposed around the circumference of the outer surface 9 of the nut 7. Accordingly, the one or more teeth 11 disposed around the outer surface of the nut 7 form the teeth 11 of a pinion 12. The one or more teeth 11 of the pinon 12 are adapted to rotatably mesh with the one or more teeth 6 of the rack 5.

Accordingly, the lever-driven plunger mechanism described herein is adapted such that, in response to a force applied to the handle 3, such a depression of the handle 3 by a finger, thumb, or hand or a user, such as in the direction of arrow 74 in FIG. 8A, the lever 2 is adapted to rotatably move from a resting position. In response, the rack 5 is adapted to move and mesh with the pinion 12 disposed on the nut 7. In response, the nut 7 is adapted to rotate in a first rotational direction, and thereby rotatably move along the thread 1 of the plunger 30. The track 1302 of the plunger 30 is adapted to engage with the rail 1301 of the injector body and thereby prevent rotation of the plunger 30 around the longitudinal axis 75. In response, the plunger 30 is adapted to move axially through the bore 40 toward the distal end 60 of the injector body 20, and thereby adapted to deliver an IOL 70 disposed within the bore 40 to an eye of a patient.

Accordingly, without limitation to theory, it will be understood that, in some implementations, the lever-driven plunger mechanism of the present disclosure is adapted to convert rotational movement of the rack 5 and pinion 12 to axial linear movement of the plunger 30, through a combination of: (1) rotational force of the nut 7 in contact with the thread 1 of the plunger 30, (2) the nut 7 being coupled to the thread 1 of the injector body 20 such that the nut 7 can rotate around the longitudinal axis 75 but not move axially relative to the injector body 20, and (3) the track 1302 disposed within the plunger 30 adapted to be axially slidably coupled with the rail 1301 disposed on the interior wall 1203 of the injector body, and thereby adapted to prevent rotation of the plunger 30 around the longitudinal axis 75.

In some implementations, for example as shown in FIG. 8A, the IOL injector 10 may include a return spring 13 having a first end 14 coupled to the lever 2 and a second end 15 coupled to the injector body 20, wherein in response to the force applied to the handle 3, the return spring 13 is adapted to return the lever 3 to the resting position. Accordingly, the return spring 13 may be adapted to rotate the lever 2 in a rotational direction opposite to that of the arrow 74. In some implementations the return spring may be a torsion spring, such as shown in FIG. 8A. In other implementations, the spring may be, for example, a compression spring, or a tension spring, among others identifiable by skilled persons upon reading the present disclosure.

In some implementations, the one or more teeth 6 of the rack 5 may be adapted to engage the one or more teeth 11 of the pinion 12 such that the rack 5 rotates the pinion 12 only in response to the movement of the lever 2 away from the resting position, such as in response to depression of the handle 3 by a user, as shown for example in the direction of arrow 74. The shape of the teeth 6/11 may be adapted to have profiles that only engage in one rotational direction, such as in the direction of the arrow 74. Accordingly, engagement of the teeth 6/11 may be adapted such that the rack 5 and the pinion 12 only move in such a way that results in axial movement of the plunger 30 toward the distal end 60 of the injector body 20. In contrast, movement of the rack 5 in a direction opposite to that of arrow 74, such as in response to movement of the lever by the return spring 13, may result in the teeth 6/11 slipping past each other and not engaging. Accordingly, the return spring 13 may return the lever 2 to the resting position without the teeth 6/11 engaging with each other.

Accordingly, as would be understood by skilled persons, in some implementations, the one or more teeth 6 of the rack 5 may form one or more pawls and the one or more teeth 11 of the pinion 12 may form a ratchet. In other implementations, the one or more teeth 6 of the rack 5 may form a ratchet and the one or more teeth 11 of the pinion 12 may form a pawl.

Figure 9B:
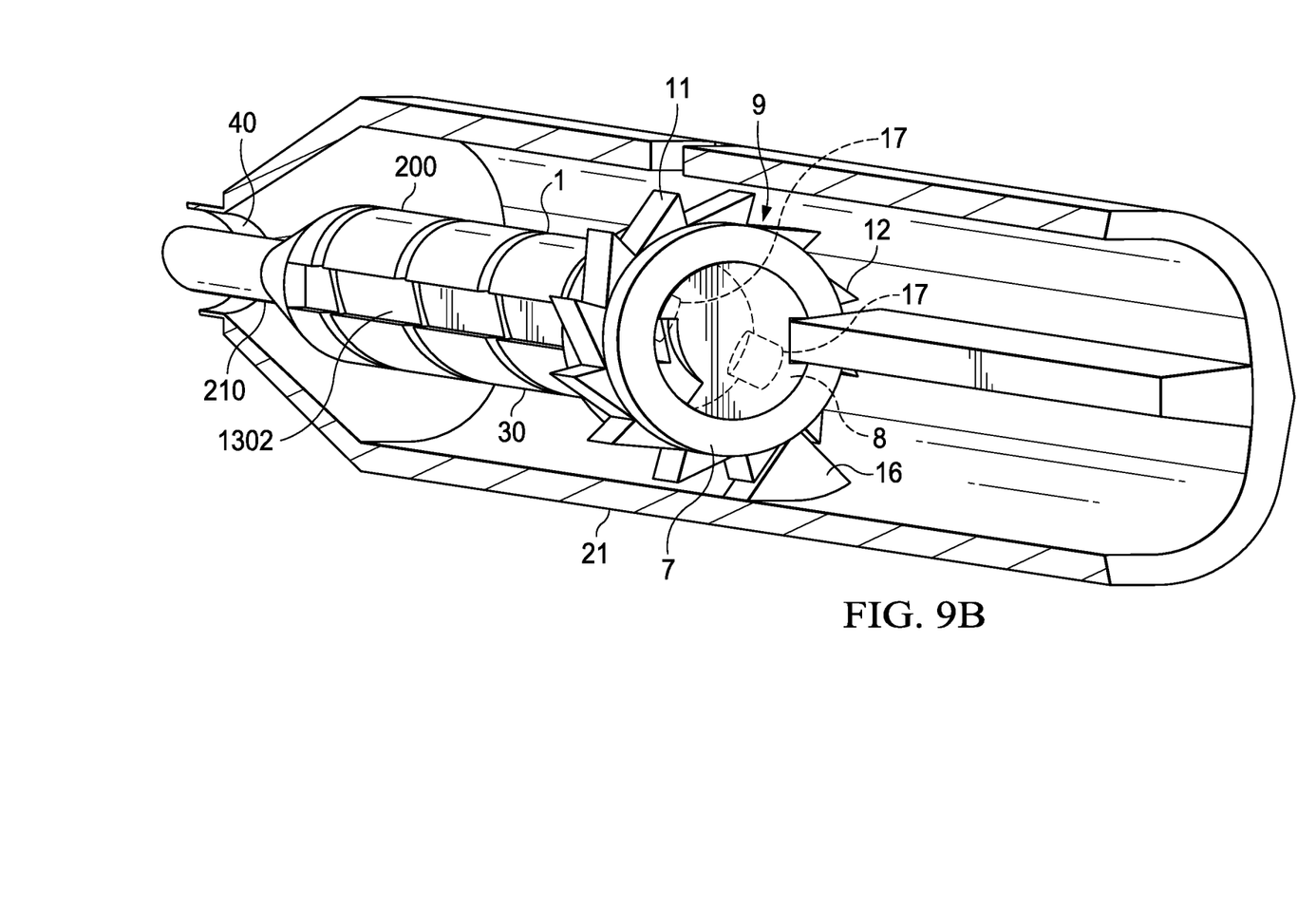
FIG. 9B is a schematic of another example plunger and plunger advancement mechanism.

In some implementations, such as shown for example in FIG. 9B, the injector body 20 may include a tooth-engaging ridge 16 adapted to contact the one or more teeth 11 of the pinion 12 and prevent rotational movement of the pinion in a second rotational direction opposite to the first rotational direction. Accordingly, similar to the ratchet described above, the tooth-engaging ridge 16 may also allow rotation of the pinion 12 only in such a way that results in axial movement of the plunger 30 toward the distal end 60 of the injector body 20.

In some implementations, the inner surface 8 of the nut 7 may include one or more thread-engaging pins 17 adapted to rotatably engage with the thread 1 of the plunger 30. For example, FIG. 9A-FIG. 9B show in schematic form a pair of thread-engaging pins 17. The dimensions of the pins 17 may be sized to fit within the dimensions of the thread 1 disposed on the plunger 30.

In some implementations, the plunger 30 may include a non-threaded portion adapted to slidably move through the nut 7 in response to an axial force applied to the plunger 30. Accordingly, in some implementations, a portion of the plunger 30 may be adapted such that the plunger 30 may axially slide through a portion of the bore 40, for example by slidable coupling of the track 1302 with the rail 1302, without the thread 1 of the plunger 30 engaging the nut 7.

In some implementations, a proximal portion of the plunger 30 may be accessible to a user, for example, such that a proximal portion of the plunger 30 extends through the proximal end 50 of the injector body 20. Accordingly, the plunger 30 may be adapted to slidably move axially in response to an axial force applied to the plunger 30, such as to the proximal portion of the plunger body 200, towards the distal end 60 of the injector body 20.

As described above, in some implementations, the injector body 20, such as the nozzle 25 of the injector body 20, may include an IOL storage location 80 configured to house an IOL 70, and an IOL dwell location 809 distal to the IOL storage location 80.

In some implementations, the IOL injector 10 described herein may be configured such that the plunger 30 further comprises a non-threaded portion adapted to slidably move through the nut 7 in response to an axial force applied to the plunger, and an IOL 70 may be axially movable from the IOL storage location 80 to the IOL dwell location 809 by axially sliding the plunger 30, and then advancing the IOL 70 axially from the IOL dwell location 809 to deliver the IOL 70 to tan eye of a patient by actuating the lever-driven plunger advancement mechanism described herein. Accordingly, in some implementations, the plunger 30 may be adapted to move axially such that the plunger tip 220 moves from a first position proximally adjacent to the IOL storage location 80 to a second position proximally adjacent to the dwell location 809 in response to an axial force applied to the plunger 30, such as an axial force applied by a user to the plunger body 200. The plunger 30 may be adapted to subsequently move axially from the second position toward the distal end 60 of the injector body in response to a force applied to the handle 3. Thus, the thread 1 may be located in an axial position within the plunger body 200 such that the thread 1 engages the nut 7 when the plunger tip 220 is in the second position proximally adjacent to the dwell location 809. The plunger 30 may be adapted such that it may then be axially movable from the second position to the distal end 60 of the injector body in response to one or more depressions of the lever 2.

In some implementations, the plunger 30 may lack a non-threaded portion. The plunger thread 1 may extend from the proximal end of the plunger 30 to the distal end of the plunger 30, such as from the proximal end of the plunger body 200 to the distal end of the plunger body 200. Accordingly, in some implementations, the plunger 30 may be adapted to move axially from a first position proximally adjacent to the IOL storage location 80 to the distal end 60 of the injector body in response to one or more depressions of the lever 2.

The lever-driven plunger mechanism described herein may be adapted such that the plunger 30 can advance axially through the bore 40 or a portion thereof to deliver an IOL 70 to an eye of a patient in response to one or more presses of the handle 3, such as 1, 2, 3, 4, 5 or more presses of the handle 3. For example, the rack 5 and pinion 12 may be adapted such that the number of teeth 6/11 have a ratio of from 1:1 to 1:5 Thus, in some implementations, the lever-driven plunger mechanism may be adapted to provide a mechanical advantage and/or axial force reduction by adapting the gear ratio of the number of teeth 6/11 of the rack 5 and/or pinion 12.

Alternatively, or in addition, in some implementations, the pitch of the thread 1 may be adapted such that the plunger 30 moves axially completely or partially through the bore 40 in response to one or more presses of the handle 3, such as 1, 2, 3, 4, 5 or more presses of the handle 3.

As would be understood by skilled persons, the term "pitch" as used herein refers to the distance from the crest of one thread to the next, wherein the flanks of a thread are the sides that connect the crest and the root. The angle of a thread is the angle between the flanks, measured in an axial plane section. The pitch of a thread is the distance, measured parallel to its axis, between corresponding points on adjacent surfaces, in the same axial plane.

In some implementations, the plunger thread 1 may have a pitch that varies along the longitudinal axis of the plunger 30.

In particular, in some implementations, the plunger thread 1 may have a pitch that is longer toward the proximal end 250 of the plunger 30 than toward the distal end of the plunger 30. A narrower pitch at the distal end of the plunger 30 may result in slower axial movement in response to a handle 3 press as the plunger 30 moves toward the distal end 60 of the injector body 20. Accordingly, in some implementations, the thread 1 may be adapted such that axial movement of the plunger 30 is slowed down during the final advancement of the IOL 70 through a distal portion of the injector body 20 and out of the IOL injector 10 and into an eye of a patient. For example, the variable pitch thread may have a pitch from, or from about, 5 to 10 mm at the distal end of the plunger 30, and may have a pitch from, or from about, 15 to 30 mm at the proximal end of the plunger 30.

In some implementations, the plunger thread 1 may have a variable pitch and the inner surface 8 of the nut 7 may include one or more pins 17 adapted to move with the variable pitch plunger thread 1.

Figure 10A:
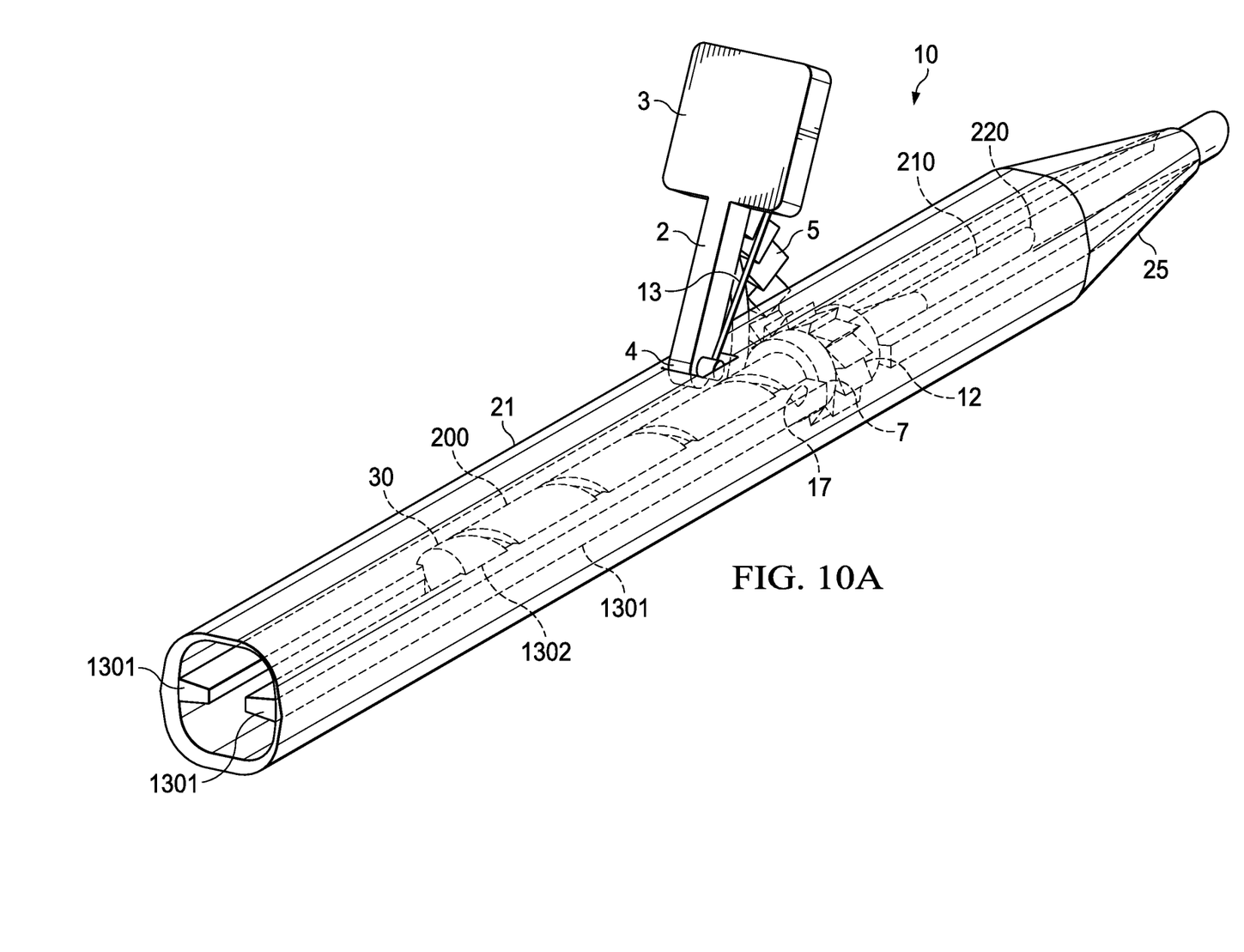
FIG. 10A is a schematic of another example IOL injector having a lever-driven plunger mechanism.
Figure 10B:
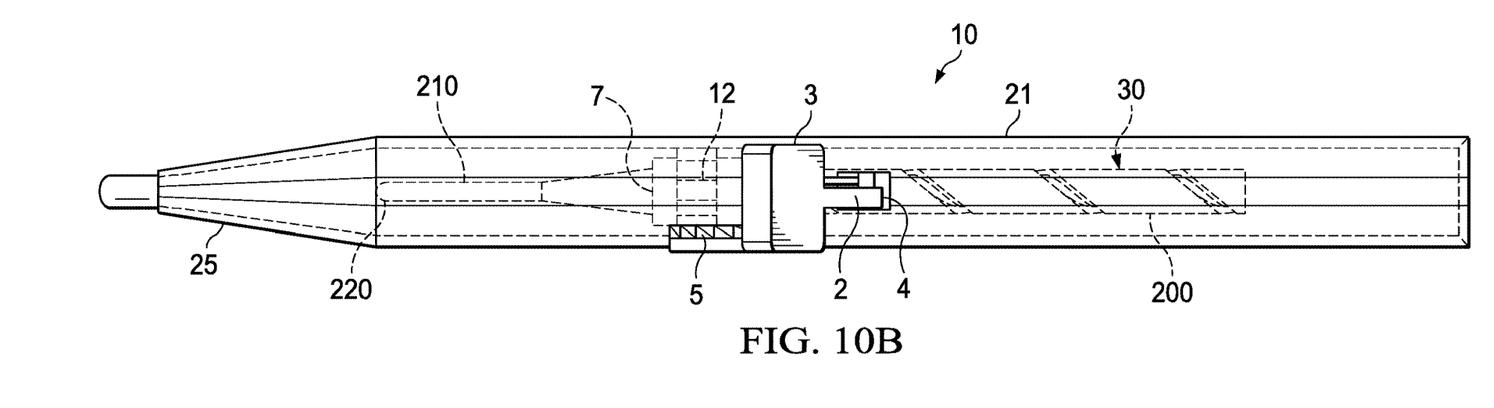
FIG. 10B is another view of the example IOL injector of FIG. 10A.
Figure 11:
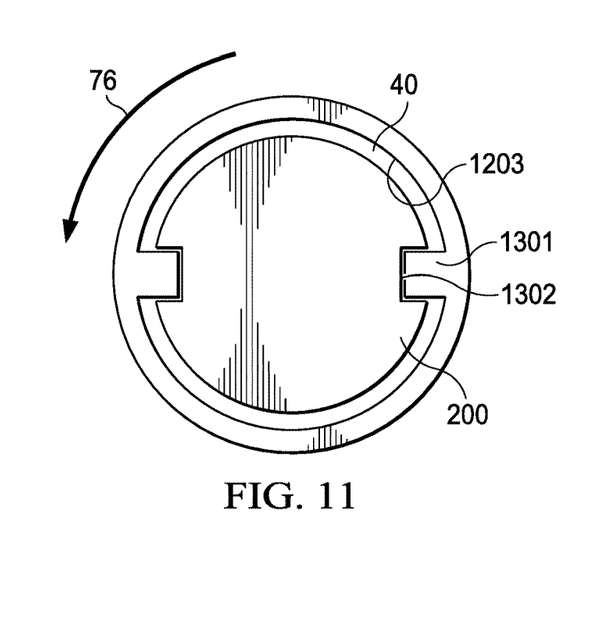
FIG. 11 is a cross-sectional view of an example IOL injector having a lever-driven plunger mechanism.

In various implementations, the IOL injector 10 may be adapted for single-handed operation by a user. The IOL injector 10 having the lever-driven plunger mechanism may be adapted to be held in a tripod grip, for example with thumb in contact with a side of the injector body 20, a middle finger on contact with the opposite side of the injector body 20, and the handle 3 of the lever 2 is adapted to be depressible by an index finger of a user. This may provide more stability for users to hold the IOL injector 10 steady during the delivery of the IOL 70 into an eye. FIG. 10A-FIG. 10B show another implementation of an IOL injector 10 wherein the handle 3 is adapted to be positioned directly above the injector body 20. In some implementations, positioning the handle 3 above the injector body 20 may allow ambidextrous use of an IOL injector 10 having the lever-driven plunger mechanism of the present disclosure.

In some implementations, the lever-driven plunger mechanism of the present disclosure may be adapted to separately inject an IOL base 461, an IOL optic 460, or both. In some implementations, the lever-driven plunger mechanism of the present disclosure may be adapted to concurrently inject an IOL base 461 and an IOL optic 460.

Non-limiting examples of IOL injectors that may be adapted according to the present disclosure include those described in U.S. Pat. No. 7,156,854 and U.S. Patent Application Publication No. 2016/0256316, the disclosures of each being incorporated herein by reference in their entireties.

Advantages of the lever-driven plunger mechanism described herein include but are not limited to the following. The lever-driven plunger mechanism described herein provides a solution to generate axial forward motion for an IOL in a smooth and controlled manner. The lever-driven plunger mechanism may be adapted to provide mechanical advantage using a lever-driven gear system to drive the plunger forward in one direction. The initial movement of the IOL to the dwell location may be achieved through sliding the plunger 30. For delivery of the IOL into the eye, using the lever-driven plunger mechanism, the IOL injector may be held in a tripod grip, also known as a pencil grip, with the user pushing the lever with their index finger, using fewer muscles than a typical syringe type grip.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens (IOL) injector having a lever-driven plunger mechanism, the IOL injector comprising:
   an injector body having:
      a bore having a longitudinal axis extending from a proximal end of the injector body to a distal end of the injector body;
      a rail disposed on an interior wall of the injector body, the rail aligned with the longitudinal axis and extending into the bore;
   a plunger movably coupled within the injector body and aligned within the bore;
   a track disposed within the plunger, the track adapted to be axially slidably coupled with the rail and adapted to prevent rotation of the plunger around the longitudinal axis;
   a lever having a first end comprising a handle accessible to a user and a second end rotatably coupled to the injector body;
   a rack having one or more teeth, the rack coupled to the lever;
   a nut coupled with the injector body such that the nut is adapted to rotate around the plunger, but not move axially relative to the injector body, the nut disposed within the bore and having:
      an inner surface adapted to rotatably couple with a thread of the plunger; and
      an outer surface having one or more teeth disposed around a circumference of the outer surface and forming a pinion, the one or more teeth of the pinon adapted to mesh with the one or more teeth of the rack;

wherein in response to a force applied to the handle:
the lever is adapted to rotatably move from a resting position;
the rack is adapted to move and mesh with the pinion disposed on the nut;
the nut is adapted to rotate in a first rotational direction, and thereby rotatably move along the thread of the plunger;
the track of the plunger is adapted to engage with the rail of the injector body and thereby prevent rotation of the plunger around the longitudinal axis; and
in response, the plunger is adapted to move axially through the bore.

2. The IOL injector of claim 1, further comprising:
a return spring having a first end coupled to the lever and a second end coupled to the injector body;
wherein in response to the force applied to the handle, the return spring is adapted to return the lever to the resting position.

3. The IOL injector of claim 1, wherein:
the one or more teeth of the rack are adapted to engage the one or more teeth of the pinion and to rotate the pinion only in response to the movement of the lever away from the resting position.

4. The IOL injector of claim 1, wherein:
the one or more teeth of the rack form one or more pawls and the one or more teeth of the pinion form a ratchet.

5. The IOL injector of claim 1, wherein:
the one or more teeth of the rack form a ratchet and the one or more teeth of the pinion form a pawl.

6. The IOL injector of claim 1, wherein:
the injector body further comprises a tooth-engaging ridge adapted to contact the one or more teeth of the pinion and prevent rotational movement of the pinion in a second rotational direction opposite to the first rotational direction.

7. The IOL injector of claim 1, wherein:
the inner surface of the nut comprises a thread adapted to rotatably engage with the thread of the plunger.

8. The IOL injector of claim 1, wherein:
the inner surface of the nut comprises one or more thread-engaging pins adapted to rotatably engage with the thread of the plunger.

9. The IOL injector of claim 1, wherein:
the plunger further comprises a non-threaded portion adapted to slidably move through the nut in response to an axial force applied to the plunger.

10. The IOL injector of claim 9, wherein:
a proximal portion of the plunger is accessible to the user;
wherein the plunger is adapted to move axially in response to the axial force applied to the plunger.

11. The IOL injector of claim 1, wherein:
the injector body further comprises an IOL storage location configured to house an IOL, and an IOL dwell location distal to the IOL storage location.

12. The IOL injector of claim 11, wherein:
the plunger further comprises a non-threaded portion adapted to slidably move through the nut in response to an axial force applied to the plunger;
the plunger is adapted to move axially from a first position proximally adjacent to the IOL storage location to a second position proximally adjacent to the dwell location in response to a continued axial force applied to the plunger; and
the plunger is adapted to move axially from the second position to the distal end of the injector body in response to a force applied to the handle.

13. The IOL injector of claim 12, wherein: the plunger is axially movable from the second position proximally adjacent to the dwell location to the distal end of the injector body in response to one or more depressions of the lever.

14. The IOL injector of claim 11, wherein:
the plunger is adapted to move axially from a first position proximally adjacent to the IOL storage location to the distal end of the injector body in response to one or more depressions of the lever.

15. The IOL injector of claim 1, wherein:
the plunger thread has a pitch that varies along the longitudinal axis of the plunger.

16. The IOL injector of claim 1, wherein:
the plunger thread has a pitch that is longer toward a proximal end of the plunger than toward a distal end of the plunger.

17. The IOL injector of claim 1, wherein:
the IOL injector is adapted for single-handed operation by the user.

18. The IOL injector of claim 1, wherein:
the IOL injector is adapted to separately inject an IOL base, an IOL optic, or both.

19. The IOL injector of claim 1, wherein:
the IOL injector is adapted to concurrently inject an IOL base and an IOL optic.

* * * * *